United States Patent [19]

Bice

[11] Patent Number: 4,468,118
[45] Date of Patent: Aug. 28, 1984

[54] METHOD AND APPARATUS FOR DETERMINING INDEX OF REFRACTION PROFILES OF OPTICAL FIBERS

[75] Inventor: Chester L. Bice, Powder Springs, Ga.

[73] Assignee: AT&T Technologies, Inc., New York, N.Y.

[21] Appl. No.: 419,645

[22] Filed: Sep. 17, 1982

[51] Int. Cl.³ ................... G01N 21/84; G01N 21/41
[52] U.S. Cl. ................... 356/73.1; 356/128
[58] Field of Search ................... 356/73.1, 128, 133, 356/338, 343

[56] References Cited

U.S. PATENT DOCUMENTS

| | | | |
|---|---|---|---|
| 2,963,938 | 12/1960 | Irland et al. | 356/343 |
| 3,705,771 | 12/1972 | Friedman et al. | 356/343 |
| 4,021,099 | 5/1977 | Kawasaki et al. | 350/96 |
| 4,197,007 | 4/1980 | Costa et al. | 356/73.1 |

OTHER PUBLICATIONS

"Precise Mesurement of the Refractive Index Profile of Optical Fibers by a Non-destructive Interference Method," Kokubun et al., Transactions of the IECE of Japan, Vol. E-60, No. 12, Dec. 1977, pp. 702-707.
"Optical Fiber Profiles Using the Refracted Near-Field Technique; A Comparison with Other Methods," Saunders, Applied Optics, vol. 20, No. 9, pp. 1645-1651, May 1, 1981.
"Mach-Zender Interferometer Data Reduction Method for Refractively in Homogenous Test Obejcts, Hunter et al., Applied Optics, vol. 14, No. 3 (Mar. 1975) pp. 634-639.
"Non-Destructive Refractive-indes Profile Measurements of Clad Optical Fibers", Marhic et al., Applied Physics Letters, vol. 26, No. 10, May 15, 1975, pp. 574-575.
"Mode Transit Times in Near-Parabolic-Index Optical Fibers" Adams et al., Electronic Letters, vol. 11, #16, Aug. 1975, pp. 389-391.
"Determination of Optical Fiber Refractive Index Profile by a Near-Field Scanning Technique", Slader et al., Applied Physics Letters, vol. 28, No. 5, Mar. 1, 1976, pp. 255-258.
"A New Technique for Measuring the Refractive Index Profiles of Graded Optical Fibers", Steward, Proc. of the Conference on Integrated Optics & Optical Communication, Japan 1977, pp. 395-98.
"Refractive Index Profile Measurement of Optical Fibers by the Refracted Near-Field Technique," Quantum Electronics, White, 3-79.
"Refracted Power Technique for Cutoff Wavelength Measurement in Single-Mode Waveguides", Bhagavatula et al., Electronic Letters, Aug. 28, 1980, vol. 16, No. 18, pp. 695-696.

*Primary Examiner*—Vincent P. McGraw
*Attorney, Agent, or Firm*—Kelley, David P.

[57] ABSTRACT

A photoconductor having a passageway therethrough is employed in practicing the refractive near-field method of determining the index of refraction profile of an optical fiber as a technique of eliminating leaky mode contribution to detected power.

9 Claims, 2 Drawing Figures

METHOD AND APPARATUS FOR DETERMINING INDEX OF REFRACTION PROFILES OF OPTICAL FIBERS

TECHNICAL FIELD

This invention relates generally to methods and apparatuses for testing optical fibers, and particularly to methods and apparatuses for determining index of refraction profiles of optical fibers of the type used as telecommunication lightguides.

BACKGROUND OF THE INVENTION

Optical fibers used today as telecommunication lightguides have a glassy, cylindrical core, encased within one or more layers of cladding, through which core light pulses are transmitted. Since the various light rays or modes of a pulse follow different paths within the core, as they reflect back and forth along the boundary of the core and cladding, the pulse length elongates during core travel thereby restricting bandwidth. To prevent this from occurring, fibers used for this purpose have been manufactured with their core having an index of refraction profile that varies radially from the core axis to the core periphery. Ideally, the distribution of refractive indices within the core should be such as to cause all light rays of a pulse to travel along the fiber at the same axial velocity regardless of traversed path length variations. In actuality some deviation from optimum refractive indes distribution of the core occurs during fiber manufacture. The manufacturer must, therefore, monitor this distribution to insure that such variations remain within specified limits.

Several methods have been developed for analyzing the index of refraction profiles of lightguides. One of the earlier, but perhaps most accurate technique, was that known as the slab method. This involves an elaborate, tedious and time consuming preparation of a fiber sample whereby a thin slice is cut from the fiber and polished to a high degree of flatness and parallelism of opposed surfaces. The samples, which are then examined with an interference microscope, act as space objects that displace in the core region the normally straight parallel fringe lines of the microscope output field. The fringe displacements or shifts are proportional to the differences in the indices of refraction within the various radial regions of the core and that of the cladding.

Non-destructive approaches have since been taken in determining profiles. Some of these are disclosed in an article by Hunter and Schreider titled "Mach-Zehnder Interferometer Data Reduction Method for Refractively Inhomogenous Test Objects", Applied Optics, Vol. 14, No. 3 (March 1975), in the article by Marhic, Ho and Epstein titled "Non-Destructive Refractive-Index Profile Measurements of Clad Optical Fibers", Applied Physics Letters, Vol. 26, (1975), and in the article by Kokubun and Iga titled "Precise Measurement of the Refractive Index Profile of Optical Fibers by a Non-Destructive Interference Method", Transactions of the IECE of Japan, Vol. E60, No. 12 (December 1977). The just-described methods, which use transverse lumination in forming interferograms, have had limited accuracy and have only been applicable to fibers having a known class of profile, for example, a parabolic profile. Recovery of the index profiles from the interferograms has also been complex. Accuracy of these methods also decrease as the number of modes increases.

As a result of the just described limitations, a simpler and more rapid method of measuring the index of refraction profile of lightguides has been developed which is known as the near-field scanning technique and which is described in the article by Sladen, Payne and Adams appearing in Applied Physics Letters, Vol. 28, No. 5, page 255 (March 1976). With this technique a short length of fiber is illuminated and the profile determined by observation of the light intensity variation across the fiber output face. This method however has limited accuracy due to the presence of leaky modes, i.e., rays that have been partially reflected from and partially refracted into the cladding, as they travel through the fiber, whose contribution cannot be accurately calculated. To overcome this limitation still another method has been devised which is known as the refracted near-field technique described in the article titled "A New Technique for Measuring the Refractive Index Profiles of Graded Optical Fibers" by W. J. Stewart that appeared in the Proceedings of the Conference on Integrated Optics and Optical Communication, Japan (1977). This technique is relatively straight forward and directly yields the refractive index profile across the entire fiber, including its cladding. The fiber dimensions, core centrality, ellipticity and numerical aperture can be determined. Good resolution is maintained throughout and both single mode and multimode fibers can be analyzed.

As opposed to the original near-field scanning method of measuring profiles the more recently developed, refracted near-field method gains its advantage by using light not trapped by the fiber core which is refracted rather than reflected. With this method a lens, having a numerical aperture substantially larger than that of the fiber, focuses a beam of light on a flat endface of a fiber and scans the focused spot across a fiber diameter. An end portion of the fiber is cleaned so that light may escape to ambience. Part of the light is guided down the fiber while the rest, refracted through an end portion of the fiber, radiates as a hollow cone outside of the fiber. The inner part of this hollow cone does still contain leaky modes, i.e. rays of light that have been partially refracted and partially reflected upon striking the fiber cladding, whose contribution to the total power radiated in the cone of light is difficult to assess. But with this newer technique the leaky modes may be excluded by placing a shield or disc in the cone to prevent the leaky modes, as well as the purely reflected modes in this inner region of the cone in which the leaky modes radiate, from reaching the photodetector situated beyond the disc. A more thorough explanation of this technique may be had by reference to the article titled "Refractive Index Profile Measurement of Optical Fibers by the Refracted Near Field Technique" by K. I. White which was published in the March 1979 issue of Optical and Quantum Electronics. A manner in which alpha ($\alpha$), the exponential value of the refractive index x-y profile function, may be determined from the light incident upon the photodetector may also be had by reference to this article.

The refractive near-field technique, however, is still not free of certain practical problems. For example, to align the end of the fiber with the scanning beam it is helpful to illuminate the fiber end with light injection into the other end of the fiber. To do this however the fiber must have substantial length and be routed through the just described disc or shield to a source of illumination. With long fibers however the cladding does not transmit light from one end to the other so that it isn't illuminated. The need for the disc itself and its precise alignment is also a handicap. Furthermore, by injecting light into the other end of a long fiber the cladding is not illuminated which renders it difficult to examine the quality of the fiber break, i.e. its degree of flatness. If a new method and apparatus could be devised that would eliminate the need for the disc, would simplify the lens system and fiber mounting, and be one in which short sample fibers could be used with the both cladding and core illuminated, a distinct advance in the art could be realized. It is the provision of such a method and apparatus to which the present invention is primarily directed.

SUMMARY OF THE INVENTION

In one form of the invention a method of determining the index of refraction profile of an optical fiber comprises the steps of positioning an end of the fiber adjacent to a photodetector having a passageway therethrough, and diametrically scanning the fiber end with a beam of light passed through an end portion of the fiber and then partially onto the photodetector about the passageway and partially through the photodetector passageway. The index of refraction profile of the fiber is derived in direct proportion to the power of light sensed by the photodetector as the light beam diametrically scans the fiber end.

In another form of the invention apparatus for use in determining the index of refraction profile of an optical fiber comprises a photodetector having a passageway therethrough, means for positioning an end of a fiber adjacent the photodetector, and means for passing a beam of light focused on the fiber end through an end portion of the fiber and then partially onto the photodetector about the passageway and partially through the passageway whereby leaky modes of light radiating in an inner portion of the beam as it conically diverges from the fiber end pass through rather than strike the photodetector.

DETAILED DESCRIPTION

Figure 1:
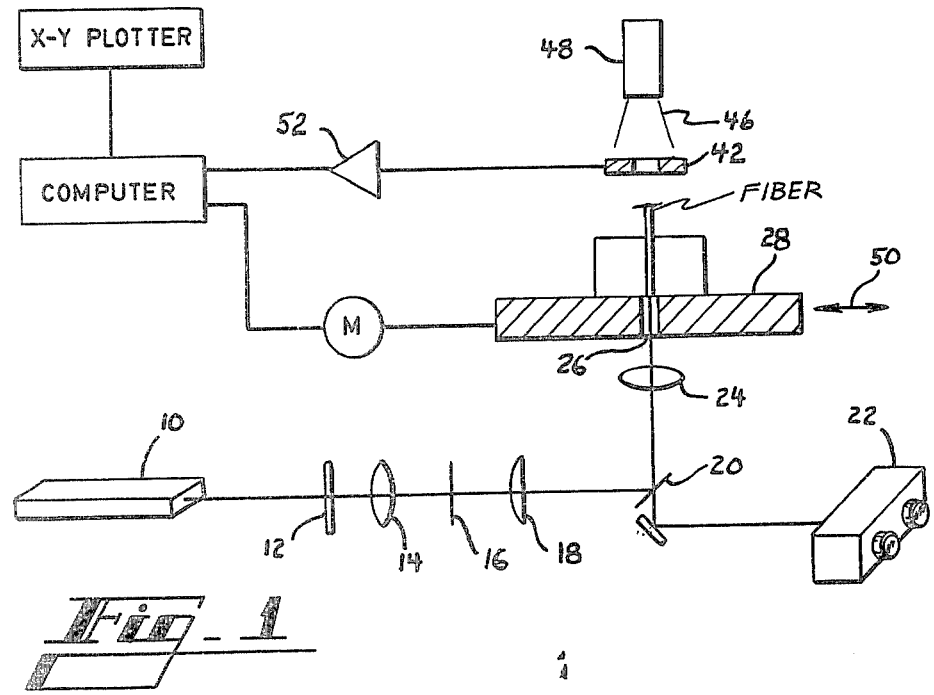
FIG. 1 is a schematic diagram of a system for measuring the index of refraction profile of an optical fiber utilizing principles of the present invention.

Referring now in more detail to the drawing, there is shown in FIG. 1 a system for measuring the index of refraction profile of an optical fiber which includes a He—Ne laser 10 that generates and projects a beam of coherent light through a quarter-wave plate 12, to minimize reflections, and a 20X objective 14 that focused the light beam within a pin hole of a pin hole plate 16. A collimating lens 18 then gathers and directs the light onto a beam splitter 20. From the beam-splitter 20 the beam is directed through a 50X 0.5 NA lens 24, through a passageway 26 in a scanning stage 28, and onto the end 40 of the fiber. From here a portion of the beam enters the fiber while another portion is reflected back through the beam-splitter and into a conventional microscope 22, such as a Leitz Diavert microscope.

Figure 2:
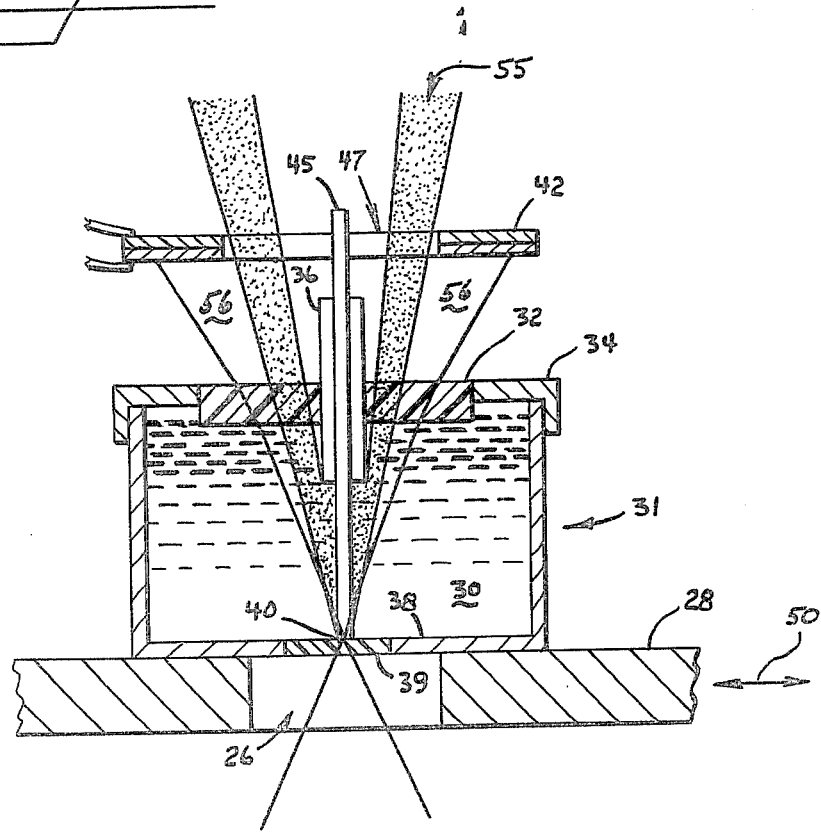
FIG. 2 is a cross-sectional view of a portion of the apparatus schematically illustrated in FIG. 1.

With reference to FIG. 2 of the drawing the fiber is seen to be mounted with fiber end 40 submerged within an index of refraction matching oil medium 30 filling a tank 31 set atop a scanning stage 28. Preferably, the index of refraction of the oil is slightly higher than the index of refraction of the fiber cladding. Tank 31 has a cap 34, a central region 32 of which is transparent through which a fiber holder 36 extends sealed to the cap. The tank has a bottom 38 formed with a central region 39 which is also transparent and against which the submerged end 40 of the fiber is positioned. From here the fiber extends upwardly through a passageway 47 that extends through the center of a disc-shaped photodetector 42 to the other fiber end 45 which lays within another beam of light 46 emitted by a conventional white light source 48. Finally, the system includes a motor M, such as a Leitz scanning stage motor, adapted to step the scanning stage 28 with incremental movement as indicated by arrows 50 in response to input signals from a computer such as a Hewlet-Packard type Model No. 9825 calculator. The output signal from the photodetector 42 is transmitted through an amplifier 52 to this computer which collects and stores the data points for comparison with an idealized profile shape. The profile derived is then recorded on an X-Y plotter coupled thereto in direct proportion to the outputs from the photodetector.

In practice a sample fiber is prepared with end 40 cut as with a diamond-type scoring brake tool. The sample is then positioned within holder 36, cap 34 placed upon tank 31, and the fiber slid into abutment with the transparent region 39 of tank floor 38. With the white light source 48 energized the fiber end 40 is observed in the field of view of microscope 22 with its axis typically appearing as a dark spot due to an axial dip in index of refraction of $\alpha$ parameter type profiles. Laser 10 is now energized and the photodetector centered over the fiber by centering the fiber holder shadow. The spot reflection of the laser from surface 39 in abutment with fiber end 40 is observed through the microscope superimposed upon the image of the fiber end. The laser spot is centered on the fiber axis and then moved along a fiber diameter to a position beyond the fiber periphery within the region of the oil 30. The computer is then activated and the power levels from the photoconductor plotted as the motor M steps the fiber so as to cause the laser spot to move relative to the fiber end across its diameter. For a more detailed explanation of this recording technique reference may be made to the article by M. J. Saunders which appears in Applied Optics, Vol. 20, No. 9, pages 1645–1651 (May 1, 1981). During the scan the leaky modes in the inner portion 55 of the laser beam pass through and thus are not detected by the photodetector while the outer portion 56 strikes the photodetector.

The just described procedure has been found to produce average percentage differences of the delta and alpha values of 3 and 7%, respectively, of those calculated by the transverse illumination method where delta is the difference between the indices of refraction of the core and cladding. This comparison was made with nine 2 inch long sample fibers having a $50\mu$ core diameter and a $125\mu$ clad diameter. A laser spot size of $<1\mu$ diameter was employed. A 1 inch diameter photodetector was used having a ½ inch diameter passageway therethrough with the photodetector located at a distance of 0.3 inches from the cap 34 and with a laser beam convergence angle of 30° formed by lens 24. The size of the photoconductor passage was slightly greater than that required to accommodate the conic, inner region that includes leaky modes, which can be calculated by application Snell's law as detailed in the previously mentioned article by K. I. White. This is true since disc sizing would be the same as passageway sizing where the disc is located on the photoconductor surface. Oversizing of the passageway is permissible since the surface area of the photoconductor remain constant throughout the scanning with only a constant change in proportionality thereby effected. For the passageway to pass all of the leaky modes in accordance with White's analysis, it must subtend an angle from the fiber end where $$\sin^2 \theta = \eta_L^2 - \eta_c^2(a) + \frac{a}{2} N^2$$

with $\eta_L$ being the index of refraction of the oil, $\eta_c$ the index of refraction of the cladding, a the core radius, $\alpha$ the profile shape parameter, previously defined, and N the numerical aperture of the fiber. As the subtended angle will depend on the distance from the fiber end, and thus also from tank 31, the photoconductor must be located at a proper distance therefrom. As taught by White the distance Z of the photoconductor from the upper surface of tank 31 may be found from the expression $$Z = \left[ \frac{D}{\sin \theta} - \frac{Z_o}{\sqrt{\eta_L^2 - \sin^2 \theta}} \cos \theta \right]$$

where $Z_o$ is the depth of the oil and D is the radius of the photoconductor passageway.

It thus is seen that a new method and apparatus is provided for use in determining the index of refraction profile of optical fibers. However, it should be understood that the just-described embodiment merely illustrates principles of the invention in one preferred form. Many modifications, additions and deletions may, of course, be made thereto without departure from the spirit and scope of the invention as set forth in the following claims.

What is claimed is:

1. The method of determining the index of refraction profile of an optical fiber comprising the steps of positioning an end of the fiber adjacent a photodetector having a passageway therethrough, diametrically scanning the fiber end with a beam of light passed through an end portion of the fiber and partially onto the photodetector about the passageway and partially through the photodetector passageway, and deriving the index of refraction profile of the fiber in direct proportion to the power of light sensed by the photodetector as the light beam diametrically scans the fiber end.

2. The method of projecting light indicative of light transmitting characteristics of an optical fiber for use in determining the index of refraction profile of the fiber which method comprises the steps of positioning an end of the fiber adjacent a photodetector having a passageway therethrough, and passing a beam of light focused on the fiber end through an end portion of the fiber adjacent the fiber end and then partially onto the photodetector about the passageway periphery and partially through the photodetector passageway so that leaky modes of light radiating in an inner portion of the beam as the beam conically diverges from the fiber end pass through rather than strike the photodetector.

3. The light projecting method of claim 2 wherein the fiber is positioned so as to extend through the photodetector passageway, and wherein said fiber end is illuminated by a second beam of light directed into the other fiber end and through the fiber.

4. Apparatus for use in determining the index of refraction profile of an optical fiber and with the apparatus comprising, in combination, a photodetector having a passageway therethrough, means for positioning an end of the fiber adjacent said photodetector, and means for passing a beam of light focused on the fiber end through an end portion of the fiber and then partially onto said photoconductor about said passageway and partially through said passageway whereby leaky modes of light radiating in an inner portion of the beam as it conically diverges from the fiber end pass through rather than strike the photodetector.

5. Apparatus in accordance with claim 4 wherein said fiber positioning means includes a tank housing an index of refraction matching oil bath in which the fiber end is submerged.

6. Apparatus in accordance with claim 5 wherein said tank has a floor at least a portion of which is transparent, and wherein said fiber positioning means further includes a scanning stage upon which said tank is supported having a light passageway therethrough over which said tank transparent floor portion is positioned.

7. Apparatus in accordance with claim 5 or 6 wherein said tank has a cap at least a portion of which is transparent through which transparent portion fiber mounting means extend.

8. Apparatus for projecting radiant energy indicative of light transmitting characteristics of an optical fiber for use in determining the index of refraction profile of the fiber and with said apparatus comprising a photodetector having a centrally located passageway therethrough; a scanning stage mounted for relative movement beneath said photodetector; a tank housing an index of refraction matching oil bath supported upon said scanning stage beneath said photodetector; means for holding an optical fiber with a fiber end within said tank submerged in said oil bath; and means for passing a beam of radiant energy focused on an end of an optical fiber held by said holding means through said fiber end and onto said photodetector with a portion of said beam passing through said photodetector passageway.

9. Light projecting apparatus in accordance with claim 8 wherein said fiber holding means includes means for holding the optical fiber in a position extending through said photodetector passageway.

* * * * *